United States Patent [19]

Temple, Jr.

[11] Patent Number: 4,950,761

[45] Date of Patent: Aug. 21, 1990

[54] (S)-[6-AMINO-4-[(1-METHYL-2-OXO-2 PHENYL-ETHYL AMINO]-5-NITRO-2-PYRIDINYL]CARBAMIC ACID, ETHYL ESTER COMPOUND

[75] Inventor: Carroll G. Temple, Jr., Birmingham, Ala.

[73] Assignee: Southern Research Institute, Birmingham, Ala.

[21] Appl. No.: 360,520

[22] Filed: Jun. 2, 1989

Related U.S. Application Data

[62] Division of Ser. No. 176,909, Apr. 4, 1988, Pat. No. 4,866,059.

[51] Int. Cl.$^5$ .................................... C07D 213/76
[52] U.S. Cl. ................................................ 546/308
[58] Field of Search ........................................ 546/308

[56] References Cited

U.S. PATENT DOCUMENTS 3,968,116  7/1976  Doherty et al. .................. 546/308
4,511,721  4/1985  Temple, Jr. et al. ............... 546/308

FOREIGN PATENT DOCUMENTS 1405308  9/1975  United Kingdom ............... 546/308

Primary Examiner—Mary C. Lee
Assistant Examiner—Zinna Northington-Davis
Attorney, Agent, or Firm—Ruth H. Newston

[57] ABSTRACT

The (2S)-(−)-isomer of (5-amino-1,2-dihydro-2-methyl-3-phenylpyrido[3,4-b]pyrazin-7-yl)carbamic acid, ethyl ester is significantly more potent than either the (2R)-(+)-isomer or the (R,S)-(±)-racemic mixture in inhibiting mitotic cell division of L1210 leukemia cells.

The compound, pharmaceutical compositions containing the compound, and a method of ameliorating cancer diseases in mammals are disclosed.

2 Claims, No Drawings

(S)-[6-AMINO-4-[(1-METHYL-2-OXO-2 PHENYL-ETHYL AMINO]-5-NITRO-2-PYRIDINYL]CARBAMIC ACID, ETHYL ESTER COMPOUND

This is a divisional of U.S. Applications Ser. No. 07/176,909 filed Apr. 4, 1988, now U.S. Pat. No. 4,866,059.

Background of the Invention

This invention relates to a compound having pharmacological activity, to compositions containing the compound, and to methods for the production and use of the compound. More particularly, the present invention concerns (2S)-(5-amino-1,2-dihydro-2-methyl-3-phenylpyrido[3,4-b]-pyrazin-7-yl)carbamic acid, ethyl ester or a pharmaceutically acceptable salt thereof, and pharmaceutical compositions containing the compound or a salt.

U.S. Pat. No. 4,450,160 discloses racemic (5-amino-1,2-dihydro-2-methyl-3-phenylpyrido[3,4-b]-pyrazin-7-yl)carbamic acid, ethyl ester as a pharmacological agent possessing antifungal and anticancer activity. D. P. Griswold, et al., *Proceedings of the AACR*, 27:306 (Abstract 1215), 1986 have shown that the compound, as a racemic mixture, demonstrates activity against L1210 leukemia, M5076 ovarian sarcoma, mouse colon tumor 36, and the vincristine-, adriamycin-, and melphalan-resistant P388 leukemias.

Summary and Detailed Description

It has been found in accordance with the present invention that the (2S)-(−) enantiomer of (5-amino1,2-dihydro-2-methyl-3-phenylpyrido-[3,4-b]pyrazin-7-yl)carbamic acid, ethyl ester possesses unexpectedly greater pharmacological activity than either the racemic mixture or the (2R)-(+) enantiomer.

The in vitro activities of (2S)-(5-amino-1,2-dihydro-2-methyl-3-phenylpyrido[3,4-b]pyrazin-7-yl)-carbamic acid, ethyl ester, the (2R)-isomer, and the racemic mixture were determined in a screen which measures the ability of a test compound to arrest cultures L1210 leukemia cells in mitotic division, and is described by G. P. Wheeler, et al., *Cancer Res.*, 42:791–798 (1982).

The test compounds were added to cultures of L1210 cells in logarithmic growth at various concentrations, and incubation of the cultures were continued. The cells were harvested, washed, and used for the preparation of microscope slides. The slides were stained with toluidine blue and 1000 cells/slide were counted and classified as interphase or mitotic. The concentration of test compound that causes a mitotic index (fraction of cells in mitosis divided by total cells) of 0.5 after an exposure of 12 hours is presented in Table 1 as $MI_{0.5}$ values.

The data in Table 1 indicate that (2S)-(5-amino-1,2-dihydro-2-methyl-3-phenylpyrido[3,4-b]-pyrazin-7yl)-carbamic acid, ethyl ester is a much more effective inhibitor of cell mitosis in cultured L1210 leukemia cells than either the (2R)-isomer or the racemic mixture of the (2R)- and )2S-isomers.

The in vivo activities of (2S)-(−)-(5-Amino-1,2-dihydro-2-methyl-3-phenylpyrido[3,4-b]pyrazin-7-yl)carbamic acid, ethyl ester, the (2R)-(+)-isomer, and the (RS)-(±)-racemic mixture against implanted P388 murine leukemia in standard laboratory mice was evaluated by the methods detailed in *Cancer Chemotherapy Reports*, 3:1–103 (1972). The values of $MI_{0.5}$ were used to estimate concentrations of each test drug which would produce lethality, as well as doses which would provide evaluable data.

Laboratory mice were inoculated intraperitoneally on Day 1 with approximately $10^6$ cells of L1210 leukemia and then injected with various doses of the drug on Days 1–5. The %T/C values at each drug dose were determined, and are reported in Table 2. The %T/C values represent the ratio of median survival

TABLE 1

Inhibition of Mitotic Cell Division of L1210 Murine Leukemia Cells

| Compound | MI0.5 (Picomolar) |
| --- | --- |
| (2S)-(−)-(5-Amino-1,2-dihydro-2-methyl-3-phenylpyrido-[3,4-b]pyrazin-7-yl)-carbamic acid, ethyl ester | 180 |
| (2R)-(+)-(5-Amino-1,2-dihydro-2-methyl-3-phenylpyrido-[3,4-b]pyrazin-7-yl)-carbamic acid, ethyl ester | 7400 |
| (R,S)-(±)-(5-Amino-1,2-dihydro-2-methyl-3-phenylpyrido-[3,4-b]pyrazin-7-yl)-carbamic acid, ethyl ester | 580 |

Note:
Multiple values indicate the results of repeated tests.

times of test (i.e. drug treated) animals to control (i.e. untreated animals) expressed as a percentage. Values of 125 %T/C are generally considered indicative of activity, while repeated values of 150 %T/C are considered confirmatory of activity.

The data in Table 2 indicates that the potency of the (2S)-isomer is significantly greater in prolonging the lives of standard laboratory animals having implanted L1210 tumors than either the (2R)-isomer or the (RS)-racemic mixture.

The present invention also includes the compounds [S-(R*,S*)]-[6-amino-4-[(2-hydroxy-1-methyl-2-phenylethyl)amino]-5-nitro-2-pyridinyl]carbamic acid, ethyl ester and (S)-[6-amino-4-[(1-methyl-2-oxo-2-phenylethyl)amino]-5-nitro-2-pyridinyl]carbamic acid, ethyl ester which are useful as intermediates for the preparation of

TABLE 2

Activity Against P388 Murine Leukemia

| Compound | Dose (mg/kg) | % T/C |
| --- | --- | --- |
| (2S)-(−)-(5-Amino-1,2-dihydro-2-methyl-3-phenylpyrido-[3,4-b]pyrazin-7-yl)-carbamic acid, ethyl ester | 0.80 | Toxic |
|  | 0.50 | 164 |
|  | 0.30 | 131 |
| (2R)-(+)-(5-Amino-1,2-dihydro-2-methyl-3-phenylpyrido-[3,4-b]pyrazin-7-yl)-carbamic acid, ethyl ester | 80 | Toxic |
|  | 50 | Toxic |
|  | 30 | 188 |
| (R,S)-(±)-(5-Amino-1,2-dihydro-2-methyl-3-phenylpyrido-[3,4-b]pyrazin-7-yl)-carbamic acid, ethyl ester | 1.00 | 171 |
|  | 0.75 | 121 |
|  | 0.50 | 123 |

(2S)-(5-Amino-1,2-dihydro-2-methyl-3-phenylpyrido-[3,4-b]pyrazin-7-yl)-carbamic acid, ethyl ester.

(2R)-, and (2S)-(5-Amino-1,2-dihydro-2-methyl-3-phenylpyrido[3,4-b]pyrazin-7-yl)carbamic acid, ethyl ester were prepared from readily available chiral agents by modification of method previously reported by C. G. Temple, et al., *J. Med. Chem.*, 26:91 (1983) and references cited therein. The method is outlined in the Reaction Sequence.

Amination of compound 1 with [S-(R*,S*)]or [R-(R*,S*)]-norephedrin, 2 or 3, in refluxing ethanol in the presence of triethylamine gave the corresponding 4-[(2-hydroxy-1-methyl-2-phenylethyl)amino]pyridines, 4 and 5. The alcohol group of the latter was oxidized with the chromium trioxidepyridine complex in methylene chloride to give the 4-[(1-methyl-2-oxo-2-phenylethyl)-amino]pyridines, 6 and 7, which, upon reductive cyclization in acetic acid in the presence of Raney nickel provided compound 8 and 9.

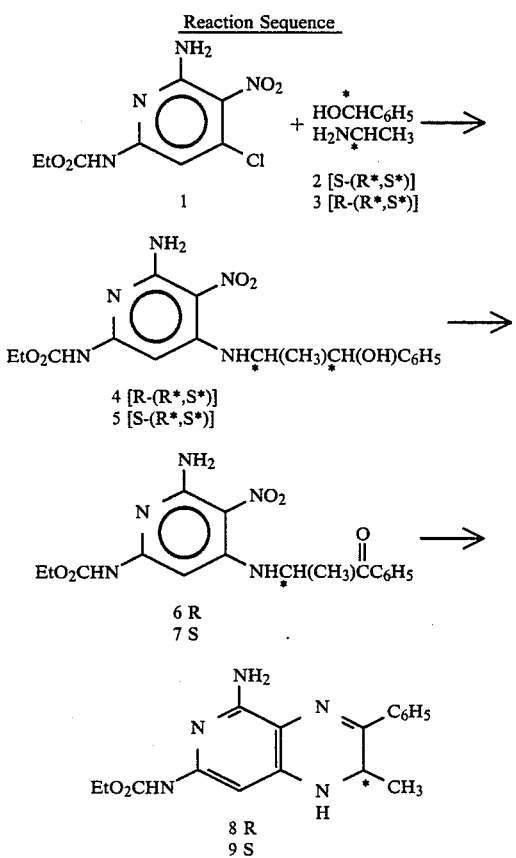

Reaction Sequence

In order to assure that homogeneous samples of each stereoisomer were prepared, all intermediates and final products were purified by flash chromatography on silica gel. At each step, measurement of the optical rotation of each pair of stereoisomeric intermediates and final products showed equal but opposite rotational values.

Attempts to separate a racemic mixture of (±)-(5-amino-1,2-dihydro-2-methyl-3-phenylpyrido-[3,4-b]pyrazin-7-yl)carbamic acid, ethyl ester using chiral chromatographic columns (Chiralcel OB®, J. T. Baker; Cyclobond II® (γ-cyclodextrin), Astec;) or a reversed-phase μBondpak® $C_{18}$ column with a mixture of α- or β-, and γ-cyclodextrins as the mobile phase were all unsuccessful. However, as illustrated by Example 3 below, the racemic mixture may successfully be resolved into the two enantiomers on a chiral EnantioPac column (α-acid glycoprotein, LKB-Produkter, Ab, Bromma, Sweden) with a mobile phase consisting of three parts 2-propanol and 97 parts of a buffer consisting of 0.05M $NaH_2PO_4$ and 0.1 M NaCl, adjusted to pH 3.0 with $H_3PO_4$. The optical purity of the individual enantiomers isolated by this method is determined from the proton magnetic resonance spectrum using the chiral chemical shift reagent (S)-(+)-2,2,2-trifluoro-1-(9-anthryl)-ethanol.

The compounds of the present invention are capable of forming salts with pharmaceutically acceptable acids. Suitable acids for use in preparing such salts form a class which is well known to the art of pharmaceutical formulation and include hydrochloric, hydrobromic, hydriodic, sulfuric, nitric, phosphoric, acetic, benzoic, citric, maleic, tartaric, succinic, gluconic, ascorbic, sulfamic, oxalic, pamoic, methanesulfonic, ethanesulfonic, 2-hydroxyethanesulfonic, benzenesulfonic, or mixtures thereof. (See, for example Berge, et al., "Pharmaceutical Salts," in *J. Pharm. Sci.*, 66:1-19 (1977). A preferred salt of the compound of this invention is the 2-hydroxyethanesulfonic (isethionate salt).

The free base form of the compounds of this invention are converted, if desired, by known methods to the corresponding acid addition salts. The salts are produced by contacting the free base form of the compounds of this invention with an equivalent amount of the desired acid in a suitable solvent such as water, an alcohol, or aqueous alcohol. The solvent is removed to yield the salt which may be used as such or further purified by recrystallization. The free base form of compounds of the present invention may be regenerated from the salts, if desired, by contacting the salt with an aqueous solution of a base such as sodium hydroxide, potassium carbonate, sodium bicarbonate, ammonia, and the like.

The free base form of compounds of this invention and their corresponding acid addition salts differ in such physical characteristics as melting point and solubility in polar solvents such as water, but are otherwise considered equivalent for the purposes of this invention.

Synthesis of the (2R)-(+) and (2S)-(−) Enantiomers of (5-Amino-1,2-dihydro-2-methyl-3-phenylpyrido-[3,4-b]- pyrazin-7-yl)carbamic Acid, Ethyl Ester Example 1

Preparation of (2R)-(+)-(5-Amino-1,2-dihydro-2-methyl-3-phenyl-pyrido[3,4-b]pyrazin-7-yl) carbamic Acid, Ethyl Ester Step 1 - Preparation of [R-(R*,S*)]-[6-Amino-4[(2-hydroxy-1-methyl-2-phenylethyl)-amino]-5-nitro-2-pyridinyl]carbamic Acid, Ethyl Ester A solution of 8.96 g (34.4 mmol) of (2-amino4-chloro-3-nitropyridin-6-yl)carbamic acid, ethyl ester, 6.49 g (42.9 mmol) of [S-(R*,S*)]-(+)-norephedrine, and 6.0 ml (4.4 g, 43 mmol) of triethylamine in 110 mL of ethanol was heated under reflux for 24 hours, after which time the reaction mixture was evaporated under vacuum.

The residue was triturated with water (200 ml) and the residue collected by filtration, washed with an additional 200 ml of water and dried in vacuum over $P_2O_5$. The dried solid was purified by flash chromatography on a 270-g column of 230-400 mesh silica gel, eluting with chloroform to give [R-(R*,S*)]-[6-amino-4-[(2-hydroxy-1-methyl-2-phenylethyl)amino]-5-nitro-2-pyridinyl]carbamic acid, ethyl ester as a yellow foam. Yield: 12.5 g (87%), mp 270°-280° C. (dec) with softening from 75° C. and foaming from 95° C. TLC (97:3 chloroform-methanol) $R_f$ 0.35.

Step 2 - Preparation of (R)-[6-Amino-4-[(1-methyl-2-oxo-2-phenylethyl)amino]-5-nitro-2-pyridinyl]carbamic Acid, Ethyl Ester Chromium trioxide (6.4 g, 64 mmol) was added to a vigorously stirred solution of pyridine (10.3 mL, 10.1 g, 128 mmol) in 265 mL of dry dichloromethane. The resulting mixture was stirred for one-half hour and the nearly-clear dark red solution was treated with a solution of 4.0 g (9.6 mmol) of [R-(R*,S*)]-[6-amino-4-[(2-hydroxy-1-methyl-2-phenylethyl)]-5-nitro-2pyridinyl]-carbamic acid, ethyl ester from Step 1 in 210 mL of dry dichloromethane.

This mixture was stirred for one hour, after which time the cloudy supernate was filtered by decantation through Celite ® and the remaining gummy residue was extracted twice with 100-mL portions of dichloromethane. The filtrate and extracts were combined and evaporated under vacuum to give a brown semisolid. Toluene (50 mL) was stripped from the semisolid under vacuum and the residue was dried under vacuum over $P_2O_5$ for one hour and then extracted with a 100-mL portion of chloroform. After filtration, the clear, brownish filtrate was concentrated to 20 mL under vacuum, and applied to a 250-g column of 230–400 mesh silica gel. The column was eluted with chloroform to yield 3.1 g (76%) of (R)-[6-amino-4-[(1-methyl-2-oxo-2-phenylethyl)amino]-5-nitro-2-pyridinyl]carbamic acid, ethyl ester as a yellow foam. Mp 150°–155° C. with softening and foaming from 100° C. TLC (97:3 chloroform-methanol) $R_f$ 0.58.

Step 3 - Preparation of (2R)-(+)-(5-Amino-1,2-dihydro-2-methyl-3-phenylpyrido[3,4-b]-pyrazin-7-yl)carbamic Acid, Ethyl Ester A solution of 1.50 g (3.59 mmol) of (R)-[6-amino-4-[(1-methyl-2-oxo-2-phenylethyl)amino]-5-nitro-2-pyridinyl]carbamic acid, ethyl ester in 75 mL of glacial acetic acid was stirred under one atmosphere of hydrogen gas in the presence of Raney nickel (4.5 g, weighed wet, washed four times with water and once with glacial acetic acid) for 3.5 hours. Although the uptake of hydrogen was only 90% of theoretical, analysis of the supernate by thin-layer chromatographic means indicated the absence of any unreduced starting material. The catalyst was removed by filtration with Celite ® and the clear green filtrate was evaporated under vacuum to give a semisolid residue. The residue was taken up in 50 mL of water and neutralized to pH 7 with 1M sodium hydroxide solution to deposit an oily semisolid. This material was extracted into chloroform (3×100 mL) with the pH of the mixture being extracted adjusted to pH 7–8 after each extraction. The organic extracts were combined, dried over sodium sulfate and evaporated under vacuum. The residue was purified by flash chromatography on a 100-g column of 230–400 mesh silica gel, eluting with 99:1 chloroform-methanol. The product was precipitated from ethanol, dried under vacuum over $P_2O_5$ to give 0.73 g of (2R)-(+)-(5-amino-1,2-dihydro-2-methyl-3-phenylpyrido[3,4-b]-pyrazin-7-yl)carbamic acid, ethyl ester. Mp >155° C. with gradual decomposition. TLC (1:1 cyclohexane-ethyl acetate) $R_f$ 0.38. $[\alpha]_D = +675° \pm 14°$ (C =0.5, methanol).

Example 2

Preparation of (2S)-(-)-(5-Amino-1,2-dihydro-2-methyl3-phenyl-pyrido3,4-b]pyrazin-7-yl)carbamic Acid, Ethyl Ester

Step 1 - Preparation of [S-(R*,S*)]-[6-Amino-4-[(2-hydroxy-1-methyl-2-phenylethyl)-amino]-5-nitro-2-pyridinyl]carbamic Acid, Ethyl Ester Employing the method from Example 1, Step 1, but using [R-(R*,S*)]-norephedrine as a starting material instead of the [S-(R*,S*)]- enantiomer, 17.9 g of [S-(R*,S*)]-[6-amino-4-[(2-hydroxy-1-methyl-2-phenylethyl)amino]-5-nitro-2-pyridinyl]carbamic acid, ethyl ester was prepared. Mp 270°–275° C. (dec) with softening from 75° C. and foaming from 95° C. TLC (97:3 chloroform-methanol) $R_f$ 0.35.

Step 2 - Preparation of (S)-[6-Amino-4-[(1-methyl-2-oxo-2-phenylethyl)amino]-5-nitro-2-pyridinyl]carbamic Acid, Ethyl Ester Using the material prepared in Example 2, Step 1 above, and the method of Example 1, Step 2 described above, 2.06 g of (S)-[6-amino-4-[(1-methyl-2-oxo-2-phenylethyl)amino]-5-nitro-2-pyridinyl ]carbamic acid, ethyl ester was prepared. Mp 150°–155° C. with softening from 85° C. and foaming from 100° C. TLC (97:3 chloroform-methanol) $R_f$ 0.58.

Step 3 - Preparation of (2S)-(-)-(5-Amino-1,2-dihydro-2-methyl-3-phenyl-pyrido[3,4-b]-pyrazin-7-yl)carbamic Acid, Ethyl Ester Using the material prepared in Example 2, Step 2 above, and the method of Example 1, Step 3 described above, 0.336 g of (2S)-(−)-(5-amino-1,2-dihydro-2-methyl-3-phenylpyrido [3,4-b]-pyrazin-7-yl)carbamic acid, ethyl ester was prepared. Mp >155° C. with gradual decomposition. TLC (97:3 cyclohexane-ethyl acetate) $R_f$ 0.38. $[\alpha]_D = -688° \pm 18°$ (C=0.5, methanol).

Example 3

Chromatographic Separation of the R and S Enantiomers of (5-Amino-1,2-dihydro-2-methyl-3-phenylpyrido[3,4-b]-pyrazin-7-yl)carbamic Acid, Ethyl Ester Baseline resolution of the enantiomers was achieved on a 0.4×10 cm chiral EnantioPac ® column ($\alpha_1$-acid glycoprotein, LKB-Produkter, Ab, Bromma, Sweden) with a mobile phase consisting of 3 parts 2-propanol and 97 parts of a buffer consisting of 0.05M $NaH_2PO_4$ and 0.1M NaCl, adjusted to pH 3 with $H_3PO_4$. For analysis, a 10-$\mu$l sample of the solution of 0.02 mg/ml of the mixed enantiomers in 10 parts of 2-propanol:90 parts of buffer is injected onto the column. At a flow rate of 0.2 ml/min (UV detection at 247 nm), the S enantiomer elutes first with a retention time of about 14.9 minutes, while the R enantiomer elutes with a retention time of about 20.9 minutes.

Nonequivalent proton magnetic resonance spectra of the R and S enantiomers are obtained throughout the use of the optically active chemical shift reagent, (S)-(+)-2,2,2,-trifluoro-1-(9-anthryl)ethanol in deuterochloroform. (See W. H Pirkle, et al., *J. Org. Chem.*, 42:384 (1977) and W. H. Pirkle, et al. *Tet. Letters,* 1966, 5849.)) The optical purity of the enantiomers separated by the method described above may be determined by this method with a detection limit of about 5%.

Example 4

Preparation of the 2-Hydroxyethanesulfonic Acid Salt of (2S)-(−)-(5-Amino-1,2-dihydro-2-methyl-3-phenyl-pyrido-3,4-b]-pyrazin-7-yl)carbamic Acid, Ethyl Ester Dowex® 50-8 ion exchange resin (700 mL, Dow Chemical Co., Midland, MI 48640) was washed with methanol, then with 0.3M hydrochloric acid, and finally with water until the washings were neutral. A solution of 28 g (0.189 mol) of 2-hydroxyethanesulfonic acid, sodium salt (isethionic acid, sodium salt) in 500 mL of water was added to the Dowex resin. The resulting mixture was stirred well and allowed to stand for 15 minutes before filtering. The resin was then washed five times with 200-mL portions of water. The filtrate and washes were combined and concentrated at 40° C. under vacuum (0.2 mm Hg) to 350 mL and the concentrate was freeze dried at 0.01 mm Hg. The resulting solid was dissolved in 500 mL and stored at 0° C. The molarity of the solution was determined by titration.

Under an atmosphere of argon gas, a methanolic solution of 4.2 g (0.0115 mol) of (2S)-(−)-(5-amino-1,2-dihydro-2-methyl-3-phenylpyrido[3,4-b]pyrazin-7-yl)carbamic acid, ethyl ester (purified by chromatography on silica gel, eluting with 2% ethanol/chloroform) is treated with 26 mL (0.095 mol) of a 0.366M solution of isethionic acid in methanol prepared as described above.

The solution was then concentrated to a foam under vacuum and stored overnight at −10° C. A mixture of the foam in 60 ml of acetonitrile was then heated to boiling, allowed to cool to room temperature, and then chilled. The bright yellow solid which formed was collected and dried at room temperature in the dark at 0.2 mm Hg for 18 hours to yield 3.35 g (63% recovery) of a 1:1.06 isethionic acid salt of the title compound, mp 168°–171° C.

Analyzed for $C_{17}H_{19}N_5O_4S$:

Calc. : C, 50.14%; H, 5.35%; N, 14.94%; S, 7.40%;
Found : C, 50.03%; H, 5.57%; N, 15.26%; S, 7.40%.

The proton magnetic resonance spectrum in dimethyl sulfoxide-$d_6$ exhibited peaks at 1.20$\delta$(doublet, 3 protons), 1.30$\delta$ (triplet, 3 protons), 2.65$\delta$ (triplet, 2 protons), 3.65$\delta$ (triplet, 2 protons), 4.25$\delta$ (quarter, 2 protons), 5.94$\delta$ (singlet, 1 proton), 7.45–7.6$\delta$ (multiplet, 3 protons), 7.7$\delta$ (singlet, 2 protons, $D_{2O}$, exchangeable), 8.1–8.2$\delta$ (multiplet, 2 protons), 8.5$\delta$ (1 proton, $D_{2O}$ exchangeable), 11.04$\delta$ (singlet, 1 proton, $D_{2O}$ exchangeable), 11.64$\delta$ (singlet, 1 proton, $D_{2O}$ exchangeable).

The infrared absorption spectrum (KBr pellet) exhibited principal absorptions at 2981, 1728, 1637, 1592, 1536, 1450, 1253, 1035, 698, and 521 reciprocal centimeters.

High-performance liquid chromatography (HPLC) analysis of the material indicated it was 99.82% pure. (Altech Econosil® C-18 column, 10 $\mu$, 0.46×25 cm, Altech Associates, 2051 Waukegan Road, Deerfield, IL 60016.) The mobile phase consisted of 40 parts acetonitrile to 60 parts of an aqueous buffer consisting of 0.05M triethylamine, adjusted to pH 3.1 with formic acid. Detection was at 247 nm, with a flow rate of 2.0 ml/min.

The optical rotation of the salt was $[\alpha]_D = -664°$ (c 0.54, methanol.)

We claim:

1. The compound having the name [S-(R*,S*)]-[6-amino-4-[(2-hydroxyl-1-methyl-2-phenylethyl)amino]-5-nitro-2-pyridinyl]carbamic acid, ethyl ester or a pharmaceutically acceptable salt thereof.

2. The compound having the name (S)-[6-amino-4-[(1-methyl-2-oxo-2-phenylethyl)amino]-5-nitro-2-pyridinyl]carbamic acid, ethyl ester or a pharmaceutically acceptable salt thereof.

* * * * *